United States Patent [19]

Roton

[11] Patent Number: 4,824,665

[45] Date of Patent: Apr. 25, 1989

[54] BARK BEETLE TREATMENT

[76] Inventor: Lary Roton, Rt. #2, Box 411, Pollock, La. 71467

[21] Appl. No.: 32,864

[22] Filed: Mar. 31, 1987

[51] Int. Cl.$^4$ ............................................. A01N 25/00
[52] U.S. Cl. ...................................... 424/84; 514/476; 514/491
[58] Field of Search .................. 424/84; 514/476, 477, 514/491

[56] References Cited

U.S. PATENT DOCUMENTS

| | | | |
|---|---|---|---|
| 2,766,554 | 10/1956 | Dorman et al. | 47/58 |
| 2,791,605 | 5/1957 | Dorman et al. | 260/500 |
| 3,068,142 | 12/1962 | Bader et al. | 167/22 |
| 3,321,364 | 5/1967 | Kessler | 167/24 |
| 3,334,012 | 8/1967 | Herschler | 167/22 |
| 4,328,206 | 5/1982 | Sprecker | 424/84 |

FOREIGN PATENT DOCUMENTS 1067634  10/1956  Fed. Rep. of Germany ...... 514/476

Primary Examiner—Leonard Schenkman
Attorney, Agent, or Firm—Hosier & Sufrin, Ltd.

[57] ABSTRACT

A method and a composition for attracting bark beetles, particularly southern pine beetles, and suppressing their further development to halt destructive forest infestations.

16 Claims, No Drawings

4,824,665

BARK BEETLE TREATMENT

BACKGROUND OF THE INVENTION

This invention relates generally to a composition and a method for suppressing bark beetle development and, more particularly, to a composition and method for preventing and controlling infestation of pine trees by southern pine beetles and associated bark beetles.

Bark beetles and particularly southern pine beetles (*Dendroctonus frontalis* Zimmerman) are endemic to many forests. When temperature, rainfall and other conditions are right, they may multiply on a prodigious scale, producing swarms of one million or more beetles per acre. As many as 100,000 to 150,000 southern pine beetles may attack successive pine trees, killing them on an epidemic scale. Although it takes 35 years to grow pine trees that are harvestable for lumber, pine bark beetles can cause devastation of pine forests in a few weeks.

Female beetles initiate the attack on each tree, producing pheromones to attract male beetles. The females bore into the tree and the pheromones guide the males to them. After each pair of beetles mates, they dig a gallery on the underside of the bark into which the female deposits up to 30 eggs. The eggs hatch into larvae roughly seven days after they are laid and the larvae feed for about two weeks producing larvae mines. The larvae then pupate in the bark for seven days and finally adults emerge from the pupa chamber by boring a small hole out through the bark. The galleries and larvae mines disrupt the cambium layer of the tree, weakening its life-support system and, by mechanisms which are not well understood, eventually kill the tree. The lumber grade and yield from beetle-killed trees are significantly reduced, particularly where harvest is delayed. In addition, the beetles carry a fungus which stains the pine wood blue, further reducing its commercial value.

Although pine trees have natural defense systems which usually limit beetle damage, when the numbers of beetles are overwhelming, the defense systems fail. It is generally agreed that the primary defense of southern pines is the preformed oleoresin system. Attacking beetles sever resin ducts, releasing their contents. The action of released compounds may be: (1) direct toxicity, (2) flow, viscosity, and crystallization characteristics that result in beetle "pitch-out", or (3) prevention of the introduction of beetle associated microorganisms that could alter tree physiology and lead to its death.

Man similarly has no effective method for handling pine beetle infestations. The application of conventional insecticides, for example, has been ineffective because it is extremely difficult to locate infested trees until the destruction has reached an advanced stage. Also, many insecticides indiscrimately harm bark beetle predators and parasites which otherwise help to naturally control the beetles.

The most common approach to controlling southern pine beetle and other bark beetle infestations has been to fell infested trees and either leave them in the forest or haul them out for salvage. This is an expensive, labor-intensive technique. Furthermore, when the diseased trees are sold for salvage, distress prices are typically the best that are available, due both to the damage to the timber and to the large quantity of such timber coming to market. In one popular alternative approach called "cut-and-leave", currently infested but still active trees and a buffer strip of uninfested trees are cut so that they fall towards the center of a grouping or "spot" of dead trees. This technique, which is intended to stop the expansion of the spot, unfortunately, is only of very limited effectiveness in controlling the spread of the beetles.

SUMMARY OF THE INVENTION

It is therefore an object of the present invention to provide a method and a composition which can be used during any season to attract bark beetles and suppress their development, including particularly a method and a composition which evokes a hypersensitive-like response to attract and suppress growth of southern pine beetles.

It is another object of the present invention to provide a method and a composition for preventing devastation of pine forests by pine bark beetles in which already infested trees need not be located or treated.

It is yet another object of the present invention to provide a method and composition for attracting emerging beetles to limited numbers of uninfested trees to significantly reduce or eliminate further beetle propagation.

A still further object of the present invention is to provide a method and composition for controlling southern pine beetles which does not harm populations of beetle parasites and predators.

It is yet another object of the present invention to provide a beetle control method and composition which induces light wood formation in treated pines.

Other objects and features of the invention will become apparent upon examination of the following specification, together with the claims. While the invention is described herein in connection with preferred or illustrative embodiments, these embodiments are not intended to be exhaustive or limiting of the invention. Rather, the invention is intended to cover all alternatives, modifications and equivalents that may be included within its sphere and scope, as defined by the appended claims.

DESCRIPTION OF THE PREFERRED EMBODIMENTS

The treatment composition used in the practice of the present invention comprises an aqueous solution of a tree penetrant and a reactant which is applied directly to pine trees along a circle near the base of the tree referred to herein as "the inoculation site." The penetrant carries the solution from the tree inoculation site up to the crown of the tree, creating a large area of treated surface below the bark. The reactant then stimulates the formation of a large area of phloem and outer xylem that both attracts beetles and then inhibits their reproduction. Shortly after inoculation, a line of clear resin, resembling tear drops, is usually observed, extending from the inoculation site to the crown of the tree.

In southern pines, a defense system, termed a "hypersensitive response," is evoked in tissues surrounding any wound, at and near the wound site. It is believed that the present invention induces a hypersensitive-like response as reflected in the noted stimulation of a large area of phloem and outer xylem in treated trees that attracts southern pine beetles in massive numbers and then severely suppresses their development.

While any compound which is capable of dissolving or otherwise carrying the reactant can be used, dimethyl sulfoxide is one penetrant which has been found to be particularly effective in the practice of the present invention. Other useful penetrants include dispersants such as organic sulfonate derivatives capable of dissolving the reactant and increasing its wettability. Also, it should be noted that while it is considerably less desirable, the reactant can be used without a penetrant. Finally, a thickening agent such as xanthan gum may optionally be used to aid application of the treatment by reducing run-off at the application site and eliminating misting.

The reactant compound used in the practice of the present invention is a compound of the formula:

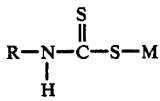

In this formula, R is a methyl or ethyl radical and M is an alkali metal, an alkaline earth metal or an ammonium radical. It is preferred that R be a methyl radical and it is yet further preferred that the reactant be sodium N-methyl dithiocarbamate.

The treatment solution is prepared by adding the appropriate amounts of the penetrant and the reactant to water and mixing. The order of addition of the components is immaterial. When a thickening agent such as xanthan gum is used, however, it is desirable to thoroughly mix the penetrant and the xantham gum before adding the reactant compound. The solution should contain from about 0 to 33% by weight of the penetrant, from about 20 to 40% by weight of the reactant, from about 0 to 4% of the thickening agent and from about 10 to 80% by weight of water. In one particularly preferred embodiment, it was found that a treatment solution containing 19% by weight dimethyl sulfoxide, 26% by weight sodium N-methyl dithiocarbamate, 3% xanthan gum and 52% by weight water was particularly effective in controlling southern pipe beetles, as described below in the examples.

The treatment solution of the present invention may be applied to the trees selected for treatment by any effective method for introducing liquids to the cambium layer and outer sapwood of a tree. For example, the treatment may be applied to the selected trees using a field axe and a syringe, sprayer or squeeze bottle. Using this method, the tree is struck with the axe at a 45° angle, with enough force to cut through the bark and cambium layer into the sapwood of the tree. The tree should be struck until a cut 3 inches long is produced. Successive 3" cuts spaced about two inches apart are made all of the way around the tree at a height of about 3 feet from the ground to establish the inoculation site. Naturally, the size and spacing of the cuts may be varied on a case by case bases, to optimize the effectiveness of the treatment.

While differing levels of the treatment may be required on a case-by-case basis, generally an application level of about 10 ppm by weight of the solution, based on the calculated dry weight of the tree, has been found to be desirable. The treatment should be applied as soon as possible after the cuts are made to insure maximum solution uptake.

In the examples below, it is shown that southern pine beetles and IPS engraver beetles preferentially select trees treated with the solution of the present invention and that the solution ultimately results in a severe reduction in these insects' progeny. In addition to southern pine beetles and IPS engraver beetles, other associates of these beetles, including turpentine beetles are attracted to the treated trees.

In addition to use in controlling beetle infestations, the present composition and method have application in trap cropping in which beetles are attracted to low value trees in forest sections marked for harvesting so that beneficial insect populations can be increased before logging operations begin. Log decks and transported infested trees would not generate new infestations near log yards.

Finally, in public wilderness areas, where beetle infestations are a threat to private forest resources, infestations can be stopped in accordance with the present invention and trees left standing for use by wildlife to regenerate the stand naturally.

To illustrate the invention, the following examples are presented.

EXAMPLES

In the examples below a treatment solution was applied by making incisions with a field axe through the tree bark and cambium layers into its sapwood and then innoculating the trees at the incisions with a syringe, sprayer, or squeeze bottle. Unless otherwise indicated, the incisions were three to six inches in length and spaced about three inches apart around the circumference of the tree, at a height of about three feet from the ground. Also, unless otherwise indicated, approximately 3 cc's of the treatment solution were applied to each incision.

EXAMPLE 1

In this example, six uninfested loblolly southern pine trees of six to nine inch DBH (diameter, breast height) were inoculated by syringe with a formulation containing one part by weight water, one part by weight dimethyl sulfoxide and four parts by weight of a 32.7% aqueous solution of sodium N-methyl dithiocarbamate. Ten days after treatment, a straight line of clear resin was observed exuding from the bark in the treated trees running from the inoculation site to the trees' crown, indicating the trees' rapid uptake of the treatment solution.

Tree No. 1

This tree was the only one not felled during the course of the test. Although beetle-free initially, ten days after inoculation, it was observed to be under attack by IPS engraver beetles, a bark beetle related to southern pine beetles. Sixty days later, the crown of the tree began yellowing, indicating that the tree was dying. At that point, bark was removed from various sections of the tree for observation. Few IPS engraver beetle pupal cells were found, with most of the brood failing to live past the larvae stage. Brood development was lower in this tree than in trees number two and three, which are discussed below.

Tree Nos. 2-3

Ten days after inoculation with the above-described treatment solution, trees 2 and 3 were felled, just above the inoculation site. Bolts, five feet in length, were cut from the lower section of each of the trees and the bolt ends were coated with molten paraffin to retard desiccation. The bolts were then placed in an upright position. Two additional five foot bolts from trees infested with southern pine beetles and IPS engraver beetles were placed in the same room as the treated uninfested bolts. Within several days, southern pine beetles and IPS engraver beetles were observed attacking the treated bolts.

After 15 days, the bark was removed from the treated bolts. Resin-soaked necrotic tissue about three inches in width was observed running vertically up the treated bolts from each of the incisions at the inoculation sites. Both IPS engraver brood and southern pine beetle brood had attacked the treated bolts in the area of the necrotic tissue as well as in adjacent areas. In parent adult egg galleries in the necrotic tissue areas, most of the eggs had failed to hatch. Those eggs in the necrotic tissue areas that did hatch produced larvae which were already dead or developing abnormally. In untreated areas, parent adult egg galleries for both the IPS engraver and the southern pine beetle looked normal, however the results set forth below in Example 4 show that these beetles are less effective in their reproduction.

Tree No. 4

Twelve days after inoculation, tree number 4 was felled and two five foot bolts were taken just above the inoculation site. In addition, an untreated tree was felled as a control, and an untreated tree with southern pine beetle in callow adult stage with brood adults emerging was felled as a bettle source. Five foot bolts were taken from these trees, and molten paraffin was applied to all of the bolt ends to retard desiccation.

Two five foot bolts infested with southern pine beetle in callow adult stage and emerging brood adults were placed in an enclosed room equidistant from the uninfested treated and untreated bolts. Within several days the beetles began selectively attacking the treated bolts. Fifteen days later, the southern pine beetles still had not attacked the control bolts whereas the treated bolts showed signs of severe attack.

Both the untreated bolts and the naturally infested bolts from which the southern pine beetle adults had emerged were then discarded. The two treated bolts were left standing for another ten days, after which the bark was removed from the two treated bolts to reveal southern pine beetle egg galleries which looked normal except at the points of entry along the necrotic strips. Few eggs had hatched, however, and where they had hatched, larvae had constructed long mines and most were dead. Although pupae and callow adults should have been present at this time, the oldest brood stage observed was mid-larvae.

Tree No. 5

Tree number 5 was cut twelve days after inoculation and two five foot bolts were taken just above the inoculation site. A healthy tree, free of pine bark beetles, was cut for a control and two five foot bolts taken from it. Ends of all bolts were coated with molten paraffin and the two treated bolts were placed at opposite corners of a screened tent, with the control bolts at the other two corners. Three bolts from infested trees with brood just starting to emerge were placed in the middle of a tent.

Within two days, southern pine beetles began emerging from the infested bolts and attacking both treated bolts. There was no attack on the control bolts, either at this point or twenty days later, as the attack on the treated bolts continued. At the twenty day point, two sixteen inch bolts were cut from each of the (now infested) treated bolts, placed in rearing cans, and the emerging beetles were collected. Upon cessation of beetle emergence, the bark was removed and the entrance holes were counted to determine the number of attacking parent adults. Only five brood adults had emerged from the four bolts.

The ratio of increase was calculated, as suggested by R. C. Thatcher and L. S. Pickard, in "Seasonal Variations in Activity of the Southern Pine Beetle in East Texas", J. Econ. Entomol. 57: 840–842, 1964. The total area of the bark was computed to be 10.6 square feet and the total number of parent adults which attacked were counted at 1,484. Since only five brood adults emerged, the ratio of increase was an extremely low 0.0034 to 1. The ratio of increase expected absent treatment, as reported in the above article, ranged from about 3 to 1 to about 1 to 1.

Tree No. 6

The above procedure was followed with tree number 6, except that only two incisions were made in this tree, about six inches in length and spaced about three inches apart. Again the selective attack of the treated bolts was observed. When sixteen inch bolts were cut from tree number 6 and placed in rearing cans, it was found that no brood emerged from any of the bolts, that there were dead parent adults in egg galleries and that very little brood made it even to the mid-larval stage.

EXAMPLE 2

Oleoresin samples were taken from five loblolly pine trees prior to treatment and again twenty days later and were frozen and then analyzed for monoterpene content.

A consistent difference was noted in all pre- and post-treatment oleoresin samples. There was an increase of a-pinene in all of the trees after treatment and a decline in B-pinene and limonene, reflecting a hypersensitive-type response.

The infusion of resin into strips in treated trees, along with the exudation of resin drops, is similar to the hypersensitive reaction produced locally from inoculated pathogens. In the treated trees the hypersensitive-type response reaction extended the entire length of the bole.

EXAMPLE 3

In early summer an attempt was made to control a one acre southern pine beetle infestation in a pine plantation with trees ranging from from 5 to 8 inches DBH.

Ten uninfested trees standing about 10 to 15 feet apart and positioned just beyond the edge of the infested section were inoculated with the treatment solution. Incisions were made as in Example 1 and the same treatment was used but it was applied with a hand sprayer rather than with a syringe. About 3 to 4 ml. of solution were applied to each incision, but due to overflow, only about 1.5 ml. remained in each wound. Uninfested trees between and around the inoculated trees were marked in order to determine whether the southern pine beetles were selectively attracted to the inoculated trees.

Sixteen days after inoculation, three out of the ten treated trees were under attack by southern pine beetles and IPS engraver beetles, but none of the marked untreated trees showed any signs of attack.

Most of the trees were removed from the area leaving one treated tree already under attack by southern pine beetle and IPS engraver beetles, another treated tree that had not been attacked, and a few untreated trees. Both southern pine and IPS beetles emerging from the tops of felled trees remaining in the area continued attacking the treated tree which was already under attack. The few beetles which attacked the other treated tree were unsuccessful in their attacks on the tree. None of the remaining untreated trees in the area were attacked.

When the treated, attacked tree was cut for observation and its bark removed, eggs which were present were not hatching, and there was very little brood development.

All of the trees treated were alive 20 months later except for those killed by beetles. Some of the trees attacked by bark beetles were still alive and in fact had put on new growth during the spring and appeared healthy. In these surviving trees, a section of bark was removed and it was found that brood had not developed. None of the untreated trees in the marked off area had been attacked by bark beetles.

EXAMPLE 4

As in Example 3, trees ahead of a small southern pine beetle infestation were treated to determine whether the infestation could be controlled by selectively attracting beetles to the treated trees. Of the 15 trees treated, after one month twelve were under attack by the beetles and none of the healthy untreated trees in the area showed any sign of beetle attack.

After another month, just before the area was clearcut, the trees were again examined, and the same treated trees were still under attack, with all of the untreated trees remaining beetle-free.

EXAMPLE 5

A southern pine beetle infested section of 17 loblolly southern pines containing a large population of overwintering southern pine beetle brood in various stages was used in this example. The DBH of the infested trees range from 5 to 14 inches.

First, a strip fifty feet wide along the sides and at both ends of the infested section of trees was marked. Trees inside the strip were flagged and treated with a hand sprayer at different times in the months of January, February and March. In this example a treatment solution comprising one part dimethyl sulfoxide and four parts of a 32.7% aqueous sodium N-methyl dithiocarbamate solution was used.

As trees in the marked area were attacked by southern pine bark beetles, turpentine beetles, and IPS engraver beetles, the dates of attack were recorded. Attacked trees were cut at different intervals and bark was removed for observation of southern pine beetle brood development and to see how the treatment affected mites, insect enemies and blue stain fungus growth.

In addition, ten treated trees with brood in late larval and pupal stages were cut at random and, for control, five untreated trees with brood in late larval and pupal stages from a remote southern pine beetle infested area were cut. Thirteen feet from the ground, a one foot bolt was cut from each tree and these bolts were placed in separate rearing cans. Emerging southern pine beetles were collected and counted, and when the emergence was complete the bark surface area of each log was measured and a 0.1 square foot circle of bark was removed from each log. As in Example 1, the number of attacks per square foot was recorded for each tree using the method of R. C. Thatcher and L. S. Pickard.

Trees treated in January, February and March all showed, twenty days after treatment, resin exuding between outer bark crevices to heights of 35 to 50 feet and on limbs over 30 feet high, demonstrating good uptake of the treatment solution.

Trees treated in January were under attack by February, but no untreated trees were under attack at this time. Trees treated in February were under attack 19 days after treatment. A close-by untreated tree was attacked, most probably by some of the few surving beetles from the treated trees.

Samples of bark were removed from this attacked untreated tree, which showed that it was heavily attacked and full of southern pine beetle parasites and predators. A large percentage of pine beetle eggs had not hatched, others had died during the early larvae stage and predators were feeding on what few brood were left.

A one foot log was cut from each of the stems at a height of 13 feet from the ground so that the emerging brood could be counted. The number of attacks per square foot for this tree was 155 and the number of brood to emerge was 14, giving a ratio of about 0.05 to 1. This indicates that even though some beetles emerged from treated trees, they were incapable of attacking healthy trees and producing a normal brood. After 12 months, the remaining trees in the marked off area were examined and none of the other untreated trees were found to have been attack.

Laboratory rearings, as reported in Table I below, showed that the ratio of emerging beetles to attacking beetles was ten times higher for the control trees in the untreated southern pine beetle infestation compared to trees in the treated infestation. Field observations also showed that the untreated southern pine beetle infestations were growing rapidly while growth of the treated infestations was stopped. The bark removed from trees in the untreated infestation showed good brood infestation while brood development in the treated trees was stopped in various different stages, eggs not hatching, early larvae dying, pupa and pre-adults dead in their cells in the mid-bark.

TABLE I

| AVERAGE BROOD DEVELOPMENT PER SQUARE FOOT OF BARK | | | |
|---|---|---|---|
| Tree No. | Attack* | Brood Emergence** | Ratio |
| A. Treated Trees | | | |
| 1 | 140 | 93 | 0.33:1 |
| 2 | 130 | 66 | 0.25:1 |
| 3 | 90 | 61 | 0.34:1 |
| 4 | 150 | 120 | 0.40:1 |
| 5 | 120 | 34 | 0.14:1 |
| 6 | 70 | 49 | 0.35:1 |
| 7 | 150 | 174 | 0.58:1 |
| 8 | 150 | 150 | 0.5:1 |
| 9 | 170 | 137 | 0.4:1 |
| 10 | 170 | 93 | 0.27:1 |
| TOTAL | 1340 | 977 | |
| MEAN | 134 | 97.7 | 0.36:1 |
| B. Control Trees | | | |
| 1 | 50 | 293 | 2.0:1 |
| 2 | 60 | 432 | 3.6:1 |
| 3 | 50 | 360 | 3.6:1 |
| 4 | 30 | 233 | 3.9:1 |
| 5 | 40 | 298 | 3.7:1 |
| TOTAL | 230 | 1616 | |
| MEAN | 46 | 323 | 3.5:1 |

*One attack equals two beetles
**Ratio of brood to parent adults

EXAMPLE 6

In mid-March, a southern pine beetle infestation containing ten trees with beetle brood was treated in the same manner and using the same treatment solution as described in Example 5. This infestation was stopped by the treatment.

EXAMPLE 7

In mid-May, a southern pine beetle infestation containing five trees with beetle brood was treated. 4% by weight Xanthan gum was introduced into the solution used in Examples 5 and 6. The solution was applied using a squeeze bottle and was found to adhere well at the innoculation site with no misting. As a result, this technique avoided wastage, facilitated handling, and prevented the applicator from coming into contact with the material. The infestation was stopped by the treatment.

EXAMPLE 8

Three treated trees were cut while southern pine beetles were in the late larvae and pupal stages and one foot bolts were taken from each tree 13 feet above where the inoculation site. The bolts were placed in individual rearing cans and known parasites and predators of southern pine beetles were collected and identified as set forth in Table II below.

The treatment did not harm the parasites and predators, and even increased their populations in certain cases, as reported in Table II below. Since it has been well documented that parasites and predators take a considerable toll on southern pine beetle populations, this illustrated an important advantage of the present invention.

TABLE II

Insect parasites and predators of *Dendroctonus frontalis* emerging from treated and untreated trees

| | Number per 929 cm² of bark surface | | | | | | | |
| | Untreated | | | | Treated | | | |
| Insect species | 1 | 2 | 3 | X | 1 | 2 | 3 | X |
| --- | --- | --- | --- | --- | --- | --- | --- | --- |
| *Lyctocoris elongatus* (Reuter) | | | | | | 0.36 | | |
| *Scolopscelis mississippensis* (Drake and Harris) | | | | | | 0.36 | | |
| *Leptacinus paurumpunctatus* (Gyllenhal) | 1.37 | 1.37 | | 0.83 | 1.6 | 2.30 | | 1.3 |
| *Platysoma parallelum* Say | | | | | | 0.37 | | |
| *Temnochila virescens* (F.) | | | | | | 0.36 | | |
| *Thanasimus dubius* (F.) | 0.68 | 1.69 | 8.51 | 3.63 | 2.8 | 0.92 | 0.37 | 1.36 |
| *Corticeus glaber* LeConte | 3.42 | 3.95 | 10.11 | 5.83 | 29.6 | 32.26 | 49.44 | 37.1 |
| *Catogenus rufus* (F.) | | | | | | | 1.6 | |
| *Aulonium ferrugineum* Zimm. | | | | | | | 3.23 | |
| *A. tuberculatum* LeConte | | 0.56 | | 0.18 | 2.4 | | 0.37 | 0.92 |
| *L. referendarious* Zimm | | | | | 0.4 | | | |
| *Cossonus corticola* Say | | | 1.06 | 0.35 | | | 2.25 | 0.75 |
| *Medetera bistriata* Parent | 0.68 | 2.82 | 1.06 | 1.52 | 1.6 | 3.26 | 1.50 | 2.12 |
| *Coeloides pissodis* (Ashmead) | 10.27 | 14.12 | 1.60 | 8.66 | 0.4 | 1.38 | 0.37 | 0.72 |
| *Dendrosoter sulcatus* Muesebeck | 0.68 | 1.13 | 2.13 | 1.31 | 4.0 | 8.76 | 0.37 | 4.38 |
| *Spathius pallidus* Ashmead | 2.82 | | | 0.94 | 0.4 | 2.76 | | 1.05 |
| *Roptrocerus xylophagorum* (Ratzeburg) | 4.79 | 7.91 | 8.51 | 7.07 | 12.04 | 31.80 | 4.12 | 16.11 |
| *Heydenia unica* Cook and Davis | | 1.13 | | | 0.8 | 1.38 | | 0.73 |
| *Rhopalicus pulchripennis* (Crawford) | 1.71 | 2.82 | 1.60 | 2.04 | | | | |

What is claimed is:

1. A method for controlling bark beetle infestations of pine trees comprising introducing into the cambium layer and outer sapwood of pine trees a solution of a tree penetrant in combination with a reactant of the formula:

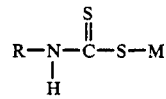

wherein R is a methyl or ethyl radical, and M is an alkali metal, an alkaline earth metal or an ammonium radical, in an amount sufficient to stimulate phloem and outer xylem in the tree to attract bark beetles and substantially reduce their progeny.

2. The method of claim 1 wherein the tree penetrant is dimethyl sulfoxide.

3. The method of claim 1 wherein the reactant is sodium N-methyl dithiocarbamate.

4. The method of claim 3 wherein the tree penetrant is dimethyl sulfoxide and the solution comprises from about 0 to 33% by weight dimethyl sulfoxide, from about 20 to 40% by weight sodium N-methyl dithiocarbamate and from about 10 to 80% by weight water.

5. The method of claim 4, including up to about 4% of a thickening agent.

6. The method of claim 5 wherein the thickening agent is xanthan gum.

7. The method of claim 1 wherein the tree penetrant is dimethyl sulfoxide, the reactant is sodium N-methyl dithiocarbamate and the solution comprises about 19% by weight dimethyl sulfoxide, about 26% by weight sodium N-methyl dithiocarbamate, about 3% xanthan gum, and about 52% by weight water.

8. The method of claim 1 wherein about 10 ppm by weight of the solution is used, based on the dry weight of each of the trees being treated.

9. The method of claim 1 wherein the tree penetrant is an organic sulfonate derivative capable of dissolving the reactant and increasing its wettability.

10. A method of inhibiting the spread of a southern pine beetle infestation comprising introducing into the cambium layer of the uninfested trees near the edge of the infestation a solution of a tree penetrant and a reactant compound of the formula:

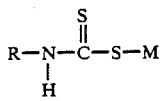

wherein R is a methyl or ethy radical, and M is an alkali metal, an alkaline earth metal or an ammonium radical, in an amount sufficient to stimulate phloem and outer xylem in the tree to attract southern pine beetles and substantially reduce their progeny.

11. The method of claim 10 wherein the tree penetrant is dimethyl sulfoxide.

12. The method of claim 10 wherein the reactant compound is sodium N-methyl dithiocarbamate.

13. A method for stimulating phloem and outer xylem in a tree to attract bark beetles and substantially reduce their progency comprising introducing into the cambium layer and outer sapwood of the trees a reactant of the formula:

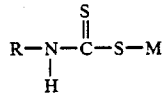

wherein R is a methyl or ethyl radical, and M is an alkali metal, an alkaline earth metal or an ammonium radical, in an amount sufficient to stimulate phloem and outer xylem in the tree to attract bark beetles and substantially reduce their progeny.

14. The method of claim 13 wherein the reactant is sodium N-methyl dithiocarbamate.

15. The method of claim 14 wherein the solution comprises about 20 to 40% by weight sodium N-methyl dithiocarbamate and the balance water.

16. The method of claim 13 in which up to about 4% of a thickening agent is used, in combination with the reactant.

* * * * *